United States Patent [19]
Bays et al.

[11] Patent Number: 5,270,333
[45] Date of Patent: Dec. 14, 1993

[54] INDOLE DERIVATIVES

[75] Inventors: David E. Bays, Ware; Alexander W. Oxford, Royston, both of England

[73] Assignee: Glaxo Group Limited, London, England

[21] Appl. No.: 745,896

[22] Filed: Aug. 16, 1991

Related U.S. Application Data

[63] Continuation of Ser. No. 643,800, Jan. 22, 1991, abandoned, which is a continuation of Ser. No. 323,945, Mar. 15, 1989, abandoned, which is a continuation of Ser. No. 7,575, Jan. 28, 1987, abandoned.

[30] Foreign Application Priority Data

Jan. 28, 1986 [GB] United Kingdom ............... 86 01959

[51] Int. Cl.⁵ .................... A61K 31/40; C07D 209/16
[52] U.S. Cl. ...................................... 514/415; 548/504
[58] Field of Search ......................................... 514/415

[56] References Cited

U.S. PATENT DOCUMENTS

| | | | |
|---|---|---|---|
| 4,636,521 | 1/1987 | Coates et al. | 514/415 |
| 4,650,810 | 3/1987 | Bays et al. | 514/415 |
| 4,816,470 | 3/1989 | Dowle | 514/415 |
| 4,994,483 | 12/1984 | Oxford et al. | 514/415 |
| 5,037,845 | 8/1991 | Oxford | 514/415 |

FOREIGN PATENT DOCUMENTS

| | | |
|---|---|---|
| 145459 | 6/1985 | European Pat. Off. |
| 3131728 | 3/1982 | Fed. Rep. of Germany |
| 2124210 | 2/1984 | United Kingdom |

OTHER PUBLICATIONS

Korolkovas Essentials of Medicinal Chem p. 99 (2nd edition) (1970).
Advances in Drug Research vol. 12 Harper et al pp. 154–168.
Binns et al Absorption & Distribution of Drugs pp. 106, 107 (1964).
Goodman & Gelman's–"The Pharmacological Basis of Therapeutics" 7th Ed. pp. 694–697 (1990).
Derwent for Dutch 68-02415 (1966).
Derwent for Dutch 67-13659 (1967).
Ferres, Drugs of Today 19, 499–501 (1968).
Orlowski, Chem Abs 92, 104269 (1980).
Bundgaard, Chem Abs 105, 102424 (1986).
Hazelton, Chem Abs 105 18235b (1986).
Bundgaard, Chem Abs 102, 209272 (1965).
Miyashita, Chem Abs 97, 162923h (1982).

*Primary Examiner*—Mark L. Berch
*Attorney, Agent, or Firm*—Bacon & Thomas

[57] ABSTRACT

Compounds are disclosed of general formula:

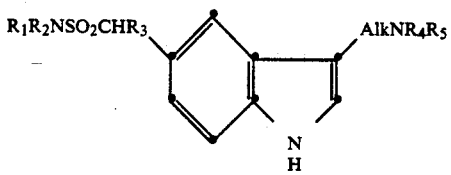

wherein $R^1$ is H, $C_{1-6}$ alkyl or $C_{3-6}$ alkenyl;
$R^2$ is H, $C_{1-3}$ alkyl, $C_{3-6}$ alkenyl, aryl, ar($C_{1-4}$)-alkylene, or $C_{5-7}$ cycloalkyl;
$R^3$ is H or $C_{1-3}$ alkyl;
$R^4$ and $R^5$ each represents H, $C_{1-3}$ alkyl or 2-propenyl, or $R^4$ and $R^5$ together form an aralkylidene group;
$R^6$ represents $-CO_2R^7$, $COR^7$, $-COCO_2R^7$, or $-CONHR^7$, where
$R^7$ represents H, $C_{1-4}$ alkyl, $C_{3-7}$ cycloalkyl, $C_{2-4}$ alkenyl, aryl or ar($C_{1-4}$)alkylene (with the provisos that (a) $R^7$ does not represent H or benzyl when $R^6$ is $-CO_2R^7$ and (b) $R^7$ does not represent alkenyl when $R^6$ is $-CONHR^7$); and Alk represents an alkylene chain containing two or three carbon atoms which may be unsubstituted or substituted by not more than two $C_{1-3}$ alkyl group, and physiologically acceptable salts and solvates (e.g. hydrates) thereof.

The compounds have potent and selective vasoconstrictor activity and are indicated as useful for the treatment of migraine. The compounds may be formulated as pharmaceutical compositions with physiologically acceptable carriers or excipients for administration by any convenient route. Various methods for the preparation of the compounds (I) are disclosed.

11 Claims, No Drawings

INDOLE DERIVATIVES

This application is a continuation of application Ser. No. 07/643,800, filed Jan. 22, 1991, abandoned which is a continuation of application Ser. No. 07/323,945, filed Mar. 15, 1989, now abandoned, which is a continuation of application Ser. No. 07/007,575, filed Jan. 28, 1987, now abandoned.

This invention relates to indole derivatives of use in the treatment of migraine, to processes for their preparation, to pharmaceutical compositions containing them and to their medical use.

The pain of migraine is associated with excessive dilatation of the cranial vasculature and known treatments For migraine include the administration of compounds having vasoconstrictor properties such as ergotamine. However, ergotamine is a non-selective vascconstrictor which constricts blood vessels throughout the body and has undesirable and potentially dangerous side effects. Migraine may also be treated by administering an analgesic, usually in combination with an antiemetic, but such treatments are of limited value.

There is thus a need for a safe and effective drug for the treatment of migraine, which can be used either prophylactically or to alleviate an established headache and a compound having a selective vasoconstrictor activity would fulfill such a role.

Furthermore, in conditions such as migraine, where the drug will usually be administered by the patient, it is highly desirable that the drug can be taken orally. It should therefore possess good bioavailability and be effectively absorbed from the gastro-intestinal tract so that prompt relief of symptoms can occur.

A wide variety cf indole derivatives have been described as being of use in the treatment of migraine. In our published UK Patent Application No. 2124210A we describe indoles of the general formula

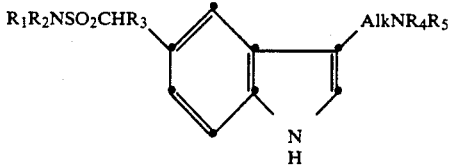

wherein $R_1$ represents a hydrogen atom or a $C_{1-6}$ alkyl or $C_{3-6}$ alkenyl group; $R_2$ represents a hydrogen atom or a $C_{1-3}$ alkyl, $C_{3-6}$ alkenyl, aryl, ar($C_{1-4}$)alkyl or $C_{5-7}$ cycloalkyl group; $R_3$ represents a hydrogen atom or a $C_{1-3}$ alkyl group: $R_4$ and $R_5$, which may be the same or different, each represents a hydrogen atom or a $C_{1-3}$ alkyl or propenyl group or $R_4$ and $R_5$ together form an aralkylidene group; and Alk represents an alkylene chain containing two or three carbon atoms which may be unsubstituted or substituted by not more than two $C_{1-3}$ alkyl groups, and physiologically acceptable salts and solvates thereof.

As indicated in UK Patent Application No. 2124210A, compounds of the above formula selectively constrict the carotid artrial bed of the anaesthetised dog and are thus potentially useful for the treatment of migraine.

Preferred compounds described in published UK Patent Application 2124210A include 3-(2-(methylamino)ethyl)-N-methyl-1H-indole-5-methanesulphonamide: 3-(2-aminoethyl)-N,N-dimethyl-1H-indole-5-methanesulphonamide; and 3-(2-aminoethyl)-N-(2-propenyl)-1H-indole-5-methanesulphonamide; and their physiologically acceptable salts and solvates, and a particularly preferred compound described in that specification is 3-(2-aminoethyl)-N-methyl-1H-indole-5-methanesulphonamide, and its physiologically acceptable salts and solvates.

In our published UK Patent Application No. 2162522A we describe a particular compound which falls within the scope of the group of compounds claimed in published UK Patent Application No. 2124210A but which is not specifically disclosed therein, namely 3-[2-(dimethylamino)ethyl]-N-methyl-1H-indole-5-methanesulphonamide, and its physiologically acceptable salts and solvates. This compound possesses a combination of highly advantageous properties for the treatment of migraine and in this respect has advantages over compounds specifically disclosed in published UK Patent Application 2124210A. Tests in anaesthetised dogs have shown that it potently and selectively constricts the carotid arterial bed following intravenous administration, and also that It is effectively and consistently well absorbed from the gastro-intestinal tract following intraduodenal administration. Its potent and selective vasoconstrictor action has also been demonstrated in vitro.

We have now found that certain 1-acyl derivatives of the above indoles exhibit highly potent and selective vasoconstrictor activity following administration to the gastro-intestinal tract.

Thus the present invention provides an indole of general formula (I):

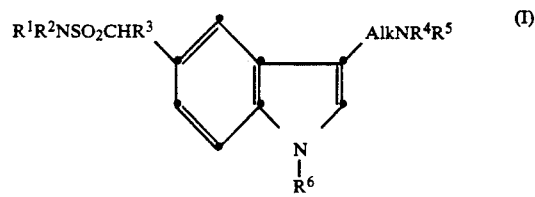

wherein $R^1$ represents a hydrogen atom or a $C_{1-6}$ alkyl or $C_{3-6}$ alkenyl group;

$R^2$ represents a hydrogen atom, a $C_{1-3}$ alkyl or $C_{3-6}$ alkenyl group, an aryl or ar($C_{1-4}$)alkylene group, or a $C_{5-7}$ cycloalkyl group:

$R^3$ represents a hydrogen atom or a $C_{1-3}$ alkyl group;

$R^4$ and $R^5$, which may be the same or different, each represents a hydrogen atom or a $C_{1-3}$ alkyl or 2-propenyl group, or $R^4$ and $R^5$ together form an aralkylidene group;

$R^6$ represents a group —$CO_2R^7$, $COR^7$, —$COCO_2R^7$, or —$CONHR^7$, where $R^7$ represents a hydrogen atom, a $C_{1-4}$ alkyl group, a $C_{3-7}$ cycloalkyl group a $C_{2-4}$ alkenyl group, or an aryl or ar($C_{1-4}$)alkylene group wherein the aryl group is preferably a phenyl group which may be unsubstituted, or substituted by a halogen atom, a $C_{1-4}$ alkyl group, a hydroxy group or a $C_{1-4}$ alkoxy group (with the provisos that (a) $R^7$ does not represent a hydrogen atom or a benzyl group when $R^6$ is the group —$CO_2R^7$ and (b) $R^7$ does not represent an alkenyl group when $R^6$ is the group —$CONHR^7$); and Alk represents an alkylene chain containing two or three carbon atoms which may be unsubstituted or substituted by not more than two $C_{1-3}$ alkyl groups and physiologically acceptable salts and solvates (e.g. hydrates) thereof.

Referring to the general formula (I) an alkyl group may be a straight or branched chain alkyl group preferably containing from 1 to 3 carbon atoms such as a methyl ethyl propyl or isopropyl group. An alkenyl group preferably contains 3 or 4 carbon atoms and may be for example, a propenyl, 2-propenyl or butenyl group. It will be appreciated that when $R^1$ or $R^2$ represents a $C_{3-6}$ alkenyl group, the double bond will not be adjacent to the nitrogen atom.

A cycloalkyl group in compounds of formula (I) preferably contains from 5 to 7 carbon atoms and may be, for example a cyclopentyl, cyclohexyl or cycloheptyl group. An aryl group, either as such or as part of an $ar(C_{1-4})$alkylene or aralkylidene group, is preferably phenyl. The alkyl moiety in an $ar(C_{1-4})$alkylene group preferably contains 1 or 2 carbon atoms. An aralkylidene group is preferably an arylmethylidene group and may be, for example, a benzylidene group.

For the substituent $R^7$, when this is a $C_{1-4}$ alkyl group, it may be for example a methyl ethyl, propyl, isopropyl or butyl group. When $R^7$ represents a $C_{3-7}$ cycloalkyl group this may be, for example a cyclopropyl, cyclopentyl or cyclohexyl group.

When $R^7$ represents a $C_{2-4}$ alkenyl group this may be for example a propenyl, butenyl or isobutenyl group. When $R^7$ represents a $phen(C_{1-4})$alkylene group, the alkyl moiety of the group may be a straight chain or branched chain alkyl moiety and is preferably a methyl or ethyl moiety. The alkyl moiety in a $C_{1-4}$ alkoxy group may be a straight or branched chain alkyl moiety and is preferably a methyl or ethyl moiety.

A preferred class of compounds represented by formula (I) is that in which $R^1$ represents a hydrogen atom or a $C_{1-6}$ alkyl group and $R^2$ represents a hydrogen atom or a $C_{1-3}$ alkyl, $C_{3-6}$ alkenyl or $ar(C_{1-4})$alkyl group.

Another preferred class of compounds of formula (I) is that in which $R^3$ represents a hydrogen atom.

A further preferred class of compounds of formula (I) is that in which $R^4$ and $R^5$, which may be the same or different, each represents a hydrogen atom or a $C_{1-3}$ alkyl group, for example a methyl or ethyl group. It is preferred that the total number of carbon atoms in $R^4$ and $R^5$ does not exceed two.

Another preferred class of compounds of formula (I) is that in which $R^6$ represents a group $-CO_2R^7$ or $-COR^7$.

A further preferred class of compounds represented by formula (I) is that in which $R^7$ represents a $C_{1-3}$ alkyl group, for example a methyl or ethyl group, or a phenyl group.

A still further preferred class of compounds falling within the scope of formula (I) is that wherein $R^1$ represents a methyl group, $R^2$ and $R^3$ both represent a hydrogen atom, $R^4$ and $R^5$ both represent a methyl group and $R^7$ represents a methyl, ethyl or phenyl group. Particularly important compounds within this group are those in which $R^6$ represents the group $-COR^7$ or $CO_2R^7$, and physiologically acceptable salts and solvates (For example hydrates) thereof.

Preferred compounds according to the invention include:

Methyl 3-[2-(dimethylamino)ethyl]-5-[[(methylamino)-sulphonyl]methyl]-1H-indole-1-carboxylate;

1-Acetyl-3-[2-(dimethylamino)ethyl]-N-methyl-1H-indole-5-methane-sulphonamide;

and physiologically acceptable salts and solates (for example, hydrates) thereof.

Suitable physiologically acceptable salts of the indoles of general formula (I) include acid addition salts formed with organic or inorganic acids for example hydrochlorides, hydrobromides sulphates, fumarates maleates and succinates. Other salts may be useful in the preparation of the compounds of general formula (I) e.g. creatinine sulphate adducts and oxalates.

We have found that compounds of the invention potently and selectively constrict the carotid arterial bed of the anaesthetised dog following intraduodenal administration, whilst having negligible effect on blood pressure. However, the compounds produce no change in carotid vascular resistance following intravenous administration and exhibit no significant vasoconstrictor activity in standard in vitro tests. It is believed that following administration to the gastro-intestinal tract compounds of the invention are converted into the corresponding 1-unsubstituted indoles i.e. they are pro-drugs for the compounds disclosed in published UK Patent Application No. 2124210A and published UK Patent Application No. 2162522A.

Compounds of the Invention are therefore useful In treating pain resulting from dilatation of the cranial vasculature, in particular migraine and cluster headache.

Compounds of the invention are suitable for oral, rectal or intranasal administration.

Accordingly the invention provides a pharmaceutical composition adapted for use in medicine which comprises at least one compound of formula (I) or a physiologically acceptable salt or solvate (e.g. hydrate) thereof and which is formulated for oral or rectal administration. Such compositions may be formulated in conventional manner using one or more pharmaceutically acceptable carriers or excipients.

The pharmaceutical compositions for oral administration may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose sucrose mannitol maize starch microcrystalline cellulose or calcium hydrogen phosphate); lubricants (e.g. stearic acid, polyethylene glycol, magnesium stearate, talc or silica); disintegrants (e.g. potato starch, sodium starch glycollate or croscarmellose sodium); or wetting agents (e.g. sodium lauryl sulphate). The tablets may be coated by methods well known in the art. Liquid preparations for oral administration may take the form of, for example, aqueous or oily solutions, syrups, elixirs, emulsions or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives, glucose/sugar syrup, gelatin, aluminium stearate gel, or hydregenated edible fats); emulsifying agents (e.g. lecithin, acacia or sorbitan mono-oleate); non-aqueous vehicles (e.g. almond oil, oily esters, ethyl alcohol or fractionated vegetable oils); and preservatives (e.g. methyl or propyl p-hydroxybenzoates or sorbic acid). The liquid preparations may also contain conventional buffers, flavouring, colouring and sweetening agents as appropriate.

For rectal administration the compounds of the invention may be formulated as suppositories or retention enemas e.g. containing conventional suppository bases such as cocoa butter or other glycerides.

A proposed dose of the compounds of the invention for administration to man (about 70 kg bodyweight) for the treatment of migraine is 1 mg to 1000 mg, for example 3 mg to 300 mg of the active ingredient per unit dose which could be administered for example 1 to 4 times per day. It will be appreciated that it may be necessary to make routine variations to the dosage depending on the age and weight of the patient, as well as the severity of the condition to be treated.

According to another aspect of the invention compounds of general formula (I) and their physiologically acceptable salts and solvates (e.g. hydrates) may be prepared by the general methods outlined hereinafter. In the following processes $R^1$, $R^2$, $R^3$, $R^4$, $R^5$, $R^6$ and Alk are as defined for the general formula (I) unless otherwise specified.

According to one general process (A), compounds of general formula (I) may be prepared by acylating a compound of general formula (II):

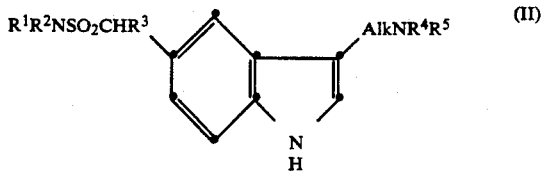

or a protected derivative thereof.

Acylating agents corresponding to the group $R^6$ which may be used in this general process include acid halides (e.g. acid chlorides such as acetyl chloride); alkyl haloformates (e.g. methyl or ethyl chloroformate): mixed or symmetrical anhydrides (e.g. acetic anhydride or benzoic anhydride); carbonates (e.g. ethyl carbonate); and isocyanates (e.g. methyl isocyanate).

The reaction is convenently effected in the presence of a base, such as an alkali metal hydride e.g. sodium or potassium hydride; an alkali metal carbonate e.g. sodium or potassium carbonate; an alkali metal alkoxide e.g. potassium t-butoxide; butyllithium; or an organic tertiary amine, e.g. triethylamine, or pyridine.

Suitable solvents which may be employed in the acylation process include amides e.g. dimethylformamide, or dimethylacetamide; ethers, e.g. tetrahydrofuran or dioxan; haloqenated hydrocarbons e.g. methylene chloride: nitriles e.g. acetonitrile and esters e.g. ethyl acetate. The reaction may conveniently be effected at a temperature In the range −10° to +150° C.

Alternatively the acylation may be effected in a two-phase reaction medium, in the presence of a phase transfer catalyst, such as tetrabutylammonium hydrogen sulphate or tetrabutylammonium bromide. Thus for example the acylating agent may be reacted with a compound of formula (II) in an inert organic solvent (e.g. a halogenated hydrocarbon such as methylene chloride), and an aqueous solution of a base (e.g. 50% sodium hydroxide) containing a phase transfer catalyst.

Compounds of general formula (II) may be prepared for example by the methods described in published UK Patent Application 2124210A.

According to a further general process (8) a compound of formula (I) according to the invention, or a salt or protected derivative thereof may he converted into another compound of the invention using conventional procedures.

For example, a compound of general formula (I) wherein one or more of $R^1$, $R^2$, $R^4$ and $R^5$ are alkyl groups may be prepared from the corresponding compounds of formula (I) wherein one or more of $R^1$, $R^2$, $R^4$ and $R^5$ represent hydrogen atoms by reaction with a suitable alkylating agent such as a compound of formula $R^cL$ where $R^c$ represents the desired $R^1$, $R^2$, $R^4$ or $R^5$ group and L represents a leaving group such as a halogen atom or a tosylate group, or a sulphate $(R^c)_2SO_4$. Thus, the alkylating agent may be for example an alkyl halide (e.g. methyl or ethyl iodide), alkyl tosylate (e.g. methyl tosylate) or dialkylsulphate (e.g. dimethylsulphate). The alkylation reaction is conveniently carried cut in an inert organic solvent such as an amide (e.g. dimethylformamide), an ether (e.g. tetrahydrofuran) or an aromatic hydrocarbon (e.g. toluene) preferably in the presence of a base. Suitable bases include, for example, alkali metal hydrides, such as sodium or potassium hydride, alkali metal amides, such as sodium amide, alkali metal carbonates such as sodium carbonate; alkali metal alkoxides such as sodium or potassium methoxide, ethoxide or t-butoxide; and tetrabutylammonium fluoride. When an alkyl halide is employed as the alkylating agent the reaction may also be carried out in the presence of an acid scavenger such as propylene or ethylene oxide. The reaction may be conveniently effected at a temperature of −20° C. to +100° C.

Compounds of formula (I) wherein $R^1$ represents a $C_{3-6}$ alkenyl group, $R^2$ represents a $C_{3-6}$ alkenyl, ar($C_{1-4}$)alkyl or $C_{5-7}$ cycloalkyl group and/or one or both of $R^4$ and $R^5$ represents propenyl may be prepared similarly using an appropriate compound of formula $R^cL$ or $(R^c)_2SO_4$.

According to another general process (C), a compound of general formula (I) according to the invention, or a salt thereof may be prepared by subjecting a protected derivative of general formula (I) or a salt thereof to reaction to remove the protecting group or groups.

Thus, at an earlier stage in the procedure for the preparation of a compound of general formula (I) or a salt thereof it may have been necessary or desirable to protect one or more sensitive groups in the molecule to avoid undesirable side reactions. For example it may be necessary to protect the group $NR^4R^5$, wherein $R^4$ and/or $R^5$ represents hydrogen, with a group easily removable at the end of the reaction sequence.

Such protection may be effected in conventional manner, for example as described In "Protective Groups In Organic Chemistry" Ed. J. F. W. McOmie (Plenum Press 1973) or "Protective Groups in Organic Synthesis" by Theodora W. Greene (John Wiley and Sons 1981). It will be appreciated that the protecting group should be one which can be removed under conditions which do not cleave the acyl group $R^6$. Thus, for example it may be an aralkyl group such as benzyl which may be cleaved by hydrogenolysis in the presence of a catalyst (e.g. palladium on charcoal).

As will be appreciated, in either of the general processes (A) or (B) described previously it may be necessary or desirable to protect any sensitive groups in the molecule as just described. Thus, a reaction step involving deprotection of a protected derivative of general formula (I) or a salt thereof may be carried out subsequent to either of the previously described processes (A) or (B).

Thus, according to a further aspect of the invention, the following reactions in any appropriate sequence may if necessary and/or desired be carried out subsequent to either of the processes (A) or (B):
(i) removal of any protecting groups; and (ii) conversion of a compound of general formula (I) or a salt thereof into a physiologically acceptable salt or solvate (e.g. hydrate) thereof.

Where it is desired to isolate a compound of the invention as a physiologically acceptable salt, for example as an acid addition salt, this may be achieved by treating the free base of general formula (I), with an appropriate acid (e.g. succinic or hydrochloric acid) preferably with an equivalent amount in a suitable solvent (e.g. aqueous ethanol).

As well as being employed as the last main step in the preparative sequence, the general methods indicated above for the preparation of the compounds of the invention may also be used for the introduction of the desired groups at an intermediate stage in the preparation of the required compound. Thus, for example, the required group at the 5-position may be introduced either before or after cyclisation to form the indole nucleus. It should therefore be appreciated that In such multi-stage processes, the sequence of reactions should be chosen in order that the reaction conditions do not affect groups present in the molecule which are desired in the final product.

The following Examples illustrate the invention. All temperatures are in ° C.

Example 1

Ethyl 3-[2-(dimethylamino)ethyl]-5-[[(methylamino)sulphonyl]methyl]-1$\underline{H}$-indole-1-carboxylate oxalate A stirred solution of 3-[2-(dimethylamino)ethyl]-N-methyl-1$\underline{H}$-indole-5-methanesulphonamide (0.5 g) in dimethylformamide (10 ml) was treated with sodium hydride (0.16 g, 80% dispersion in oil) and stirred for 0.5 h at room temperature. The solution was cooled to 0° and ethyl chloroformate (0.183 g, 0.16 ml) was added dropwise. The mixture was stirred for 1 h at room temperature, quenched with sodium bicarbonate (20 ml) and extracted with ethyl acetate (3×30 ml). The organic extracts were washed with brine (2×30 ml), dried (MgSO$_4$) and concentrated in vacuo to give an oil (0.45 g) which was purified by short path chromatography (Merck silica 7747, 20 g) eluting with dichloromethane:ethanol:ammonia (100:8:1) to give a solid (0.24 g) which was triturated with diethyl ether (20 ml) to give a powder (0.143 g). The powder was dissolved in hot ethanol (5 ml) and heated with a hot solution of oxalic acid (38 mg) in ethanol (1 ml). The solution was allowed to cool and the crystals that formed were collected and dried at 60° in vacuo to give the title compound (0.130 g) m.p. 197°-198° C.

T.l.c. Silica (dichloromethane:ethanol:ammonia=50:8:1) Rf 0.8 detection u.v., KMnO$_4$ Analysis Found: C,49.8;H,6.4;N,8.8.

$C_{17}H_{25}N_3O_4S \cdot C_2H_2O_4 \cdot 0.14$ H$_2$O requires: C,49.6;H,6.0;N,9.1%.

H$_2$O analysis: 0.55% water content≡0.14 mol H$_2$O.

Example 2

Methyl 3-[2-(dimethylamino)ethyl]-5-[[(methylamino)sulphonyl]methyl]-1$\underline{H}$-indole-1-carboxylate oxalate A solution of 3-[2-(dimethylamino)ethyl]-N-methyl-1$\underline{H}$-indole-5-methane sulphonamide (1.0 g), in dimethylformamide (50 ml) was added to sodium hydride (0.2 g, 80% dispersion in oil) under a nitrogen atmosphere to give a suspension which was stirred for 2 h at room temperature then cooled to 5°. Methyl chloroformate (0.32 g, 0.26 ml), in tetrahydrofuran (5 ml) was added dropwise with cooling over 10 min. The reaction mixture was stirred for a further 1 h at 5° and then poured into a mixture of chloroform (50 ml) and saturated ammonium chloride (50 ml). The chloroform layer was concentrated in vacuo, dissolved in ethyl acetate (50 ml) and backwashed with saturated brine (250 ml). The organic layer was evaporated in vacuo to give a solid which was purified by chromatography (activated alumina 90 Merck 45 g), eluting with dichloromethane:methanol (98:2). The appropriate fractions were combined and evaporated in vacuo to give the 1-acetyl derivative as a solid. The solid (0.445 g) was dissolved in hot absolute ethanol and treated with oxalic acid (113 mg) in methanol. The crystals (0.43 g) that formed were recrystallised from methanol (20 ml) and dried in vacuo to give the title compound (0.3 g) as a powder m.p. 185°-186°.

T.l.c. Silica dichloromethane:ethanol:ammonia 50:8:1 Rf 0.5 detection u.v. IPA KMnO$_4$.

Analysis Found: C,48.6; H,5.7; N,9.3.

$C_{16}H_{23}N_3O_4S \cdot C_2H_2O_4$ requires: C,48.4; H,5.7; N,9.4%.

Example 3

1-Acetyl-3-[2-(dimethylamino)ethyl]-N-methyl-1$\underline{H}$-indole-5-methane-sulphonamide hemioxalate A solution of 3-]2-(dimethylamino)ethyl]-N-methyl-1$\underline{H}$-indole-5-methane sulphonamide (1.0 g) in dimethylformamide (50 ml) was added to sodium hydride (0.2 g, 80% dispersion in oil) under a nitrogen atmosphere to give a suspension which was stirred For 2 h, then cooled to 5°. Acetyl chloride (0.26 g) in tetrahydrofuran (5 ml) was added dropwise over 15 min, maintaining the temperature below 5°. The reaction mixture was stirred for a further 1 h, and then poured into a mixture of chloroform (50 ml) and saturated ammonium chloride (50 ml). The chloroform layer was concentrated in vacuo, dissolved in ethyl acetate (50 ml) and backwashed with saturated brine (250 ml). The organic layer was evaporated in vacuo and the resulting solid was triturated with diethyl ether (250 ml) to give a powder (0.44 g) which was dissolved in ethanol (25 ml), treated with oxalic acid (119 mg) in methanol (25 ml) and dried in vacuo to give the title compound (0.15 g) as a solid m.p. 208°-210°.

T.l.c. Silica dichloromethane:ethanol:ammonia 50:8:1 RF 0.6

Analysis Found: C,52.4; H,6.3; N,10.4

$C_{16}H_{23}N_3O_3S \cdot 0.5C_2H_2O_4 \cdot 0.3H_2O$ requires: C,52.7; H,6.3; N,10.8.

H$_2$O Assay indicates 1.28% H$_2$O=0.3 mol H$_2$O.

Example 4

1-Benzoyl-3-[2-(dimethylamino)ethyl]-N-methyl-1$\underline{H}$-indole-5-methanesulphonamide oxalate Benzoic acid anhydride (0.382 g) was dissolved in pyridine (5 ml), cooled to −5° and treated dropwise with a solution of 3-[2-dimethylamino)ethyl]-N-methyl-1$\underline{H}$-indole-5-methanesulphonamide (0.5 g) in pyridine under nitrogen. The solution was heated at reflux for 2 h, treated with saturated ammonium chloride and extracted with ethyl acetate. The organic phase was separated and concentrated in vacuo to give an oil which was purified by chromatography (Merck Silica 9385) and eluted with a mixture of dichloromethane: ethanol:ammonia (150:8:1). The appropriate fractions were combined and concentrated in vacuo to give a solid (0.1 g) which was dissolved in ethanol (20 ml) and treated with oxalic acid (31 mg, 1 equivalent) in methanol (2 ml). The crystals that formed were collected and dried at 70° in vacuo for 18 h to give the title compound (0.075 g) as a solid m.p. 205°–208°.

T.l.c. Silica dichloromethane:ethanol:ammonia 150:8:1 RF 0.3 detection IPA, KMnO$_4$ Assay Found: C,56.2; H,5.6; N,8.2.

$C_{21}H_{25}N_3O_3S \cdot C_2H_2O_4 \cdot 0.2H_2O$ requires C,56.0; H,5.6; N,8.5%.

H$_2$O assay contains 0.76 H$_2$O w/w=0.2 mol H$_2$O

The following example illustrates a pharmaceutical formulation according to the invention containing 1-acetyl-3-[2-(dimethylamino) -ethyl]-N-methyl-1H-indole-5-methanesulphonamide hemioxalate as the active ingredient. Other compounds of the invention may be formulated in a similar manner.

| Tablets for Oral Adminisration | |
|---|---|
| | mg/tablet |
| Active Ingredient | 100 |
| Magnesium stearate BP | 1.0 |
| Anhydrous lactose | 99 |

The active ingredient is sieved and blended with the anhydrous lactose and magnesium stearate. The mix is then compressed into tablets using a Manesty F3 tablet machine fitted with 8.0 mm concave punches.

We claim:

1. A pharmaceutical composition comprising at least one compound of formula (I):

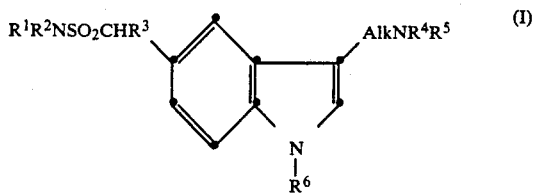

wherein R$^1$ represents a hydrogen atom or a C$_{1-6}$alkyl or C$_{3-6}$alkenyl group; R$^2$ represents a hydrogen atom, a C$_{1-3}$alkyl or C$_{3-6}$alkenyl group, an aryl, substituted aryl, aryl(C$_{1-4}$)alkylene, or substituted aryl(C$_{1-4}$)alkylene group, or a C$_{5-7}$cycloalkyl group;

R$^3$ represents a hydrogen atom of a C$_{1-3}$alkyl group;

R$^4$ and R$^5$, which may be the same or different, each represents a hydrogen atom or a C$_{1-3}$alkyl or 2-propenyl group, or R$^4$ and R$^5$ together form an aralkylidene or a substituted aralkylidene group;

R$^6$ represents a group —CO$_2$R$^7$, —COR$^7$, —COCO$_2$R$^7$, or —CONHR$^7$, where R$^7$ represents a hydrogen atom, a C$_{1-4}$alkyl group, a C$_{3-7}$cycloalkyl group, a C$_{2-4}$alkenyl group, or an aryl, substituted aryl, aryl(C$_{1-4}$)alkylene, or substituted aryl(C$_{1-4}$)alkylene group (with the provisos that (a) R$^7$ does not represent a hydrogen atom or a benzyl group when R$^6$ is the group —CO$_2$R$^7$, and (b) R$^7$ does not represent an alkenyl group when R$^6$ is the group —CONHR$^7$); and Alk represents an alkylene chain containing two or three carbon atoms which may be unsubstituted or substituted by not more than two C$_{1-3}$alkyl groups; and wherein the aryl moiety is a phenyl group and the substituted aryl group may be substituted by a halogen atom, a C$_{1-4}$alkyl group, a hydroxy group or a C$_{1-4}$alkoxy group;

and physiologically acceptable salts and hydrates thereof, together with a physiologically acceptable carrier or excipient therefor.

2. A composition according to claim 1, wherein, in formula (I) R$^1$ represents a hydrogen atom or a C$_{1-6}$alkyl group and R$^2$ represents a hydrogen atom or a C$_{1-3}$alkyl, C$_{3-6}$alkenyl or ar(C$_{1-4}$)alkyl group.

3. A composition according to claim 1, wherein, in formula (I), R$^3$ represents a hydrogen atom.

4. A composition according to claim 1, wherein, in formula (I), R$^4$ and R$^5$, which may be the same or different, each represents a hydrogen atom or a C$_{1-3}$alkyl group.

5. A composition according to claim 1, wherein, in formula (I), R$^7$ represents a C$_{1-3}$alkyl group or a phenyl group.

6. A composition according to claim 1, wherein in formula (I), the aryl moiety is a phenyl group or a substituted phenyl group which may be substituted by a halogen atom, a C$_{1-4}$alkyl group, a hydroxy group or a C$_{1-4}$alkyoxy group.

7. A composition according to claim 1, wherein, in formula (I), R$^6$ represents a group —CO$_2$R$^7$ or —COR$^7$, where R$^7$ is as defined in claim 1.

8. A composition according to claim 1, wherein, in formula (I), R$^1$ represents a methyl group, R$^2$ and R$^3$ both represent a hydrogen atom, R$^4$ and R$^5$ both represent a methyl group and R$^7$ represents a methyl, ethyl or phenyl group.

9. A composition according to claim 8, wherein, in formula (I), R$^6$ represents a group —CO$_2$R$^7$ or —COR$^7$, where R$^7$ is a hydrogen atom, a C$_{1-4}$alkyl group, a C$_{3-7}$cycloalkyl group, a C$_{2-4}$alkenyl group, or an aryl or ar(C$_{1-4}$)alkylene group (with the provisos that (a) R$^7$ does not represent a hydrogen atom or a benzyl group when R$^6$ is the group —CO$_2$R$^7$, and (b) R$^7$ does not represent an alkenyl group when R$^6$ is the group —CONHR$^7$).

10. A composition according to claim 1 selected from methyl-3-[2-(dimethylamino)ethyl]5-[[(methylamino)-sulphonyl]-methyl]-1H-indole-1-carboxylate; 1-acetyl-3-[2-(dimethylamino)ethyl]-N-methyl-1H-indole-5-methane-sulphonamide; and physiologically acceptable salts and solvates thereof.

11. A method of treating a patient susceptible to or suffering from migraine which comprises administering to the patient an effective amount of a pharmaceutical composition according to claim 1.

* * * * *